(12) United States Patent
Narayan et al.

(10) Patent No.: US 8,110,036 B2
(45) Date of Patent: Feb. 7, 2012

(54) MOISTURE CURABLE OIL AND FAT COMPOSITIONS AND PROCESSES FOR PREPARING THE SAME

(75) Inventors: Ramani Narayan, Okemos, MI (US); Daniel Graiver, Midland, MI (US); Kenneth W. Farminer, Midland, MI (US); Madhusudhan Srinivasan, Okemos, MI (US)

(73) Assignees: Board of Trustees of Michigan State Univeristy, East Lansing, MI (US); Bioplastic Polymers and Composites, LLC, Okemos, MI (US)

( * ) Notice: Subject to any disclaimer, the term of this patent is extended or adjusted under 35 U.S.C. 154(b) by 674 days.

(21) Appl. No.: 12/287,100

(22) Filed: Oct. 6, 2008

(65) Prior Publication Data

US 2010/0083871 A1    Apr. 8, 2010

(51) Int. Cl.
*C09D 191/00* (2006.01)
*C08L 91/00* (2006.01)
*C07F 7/08* (2006.01)

(52) U.S. Cl. .............. 106/244; 106/287.13; 106/287.14; 106/287.15; 106/287.16; 106/252; 554/77

(58) Field of Classification Search .................. 106/244, 106/252, 287.13–287.16; 554/77
See application file for complete search history.

(56) References Cited

U.S. PATENT DOCUMENTS

| | | | |
|---|---|---|---|
| 2,717,900 A | 9/1955 | Plueddemann | |
| 2,735,825 A | 2/1956 | Kress | |
| 3,294,739 A | 12/1966 | Weyenberg | |
| 3,334,067 A | 8/1967 | Weyenberg | |
| 3,383,355 A | 5/1968 | Cooper | |
| 3,424,598 A | 1/1969 | Snyder et al. | |
| 3,856,839 A | 12/1974 | Smith et al. | |
| 3,997,485 A | 12/1976 | Dowbenko et al. | |
| 4,512,926 A | 4/1985 | Kampf | |
| 6,265,516 B1 | 7/2001 | Okawa et al. | |
| 6,380,316 B1 * | 4/2002 | Bahadur et al. | 525/263 |
| 7,176,269 B2 | 2/2007 | Hakuta et al. | |
| 7,307,134 B2 * | 12/2007 | Lim et al. | 528/34 |
| 2004/0116639 A1 | 6/2004 | Lim et al. | |

FOREIGN PATENT DOCUMENTS

BE        510419        8/1952

OTHER PUBLICATIONS

T. Nabuurs et al., Prog. in Org. Coating 27, 163 (1996).
Biermann et al. in Angew. Chem. Int. Ed. 39, 2206 (2000).
International Preliminary Report on Patentability for PCT/US2009/005489, dated Dec. 11, 2009.

* cited by examiner

*Primary Examiner* — David M Brunsman
(74) *Attorney, Agent, or Firm* — Dickinson Wright PLLC

(57) ABSTRACT

A moisture-curable, silane-modified oil is disclosed. The silane-modified oil includes an unsaturated oil having at least one unsaturated aliphatic hydrocarbon chain per molecule of the unsaturated oil, and at least one hydrolysable silyl group grafted to the unsaturated aliphatic hydrocarbon chain. The silane-modified oil has a degree of unsaturation that is substantially similar that of the unsaturated oil. A process for forming the moisture-curable, silane-modified oil according to the disclosure includes reacting the unsaturated oil with an unsaturated hydrolysable silane in the presence of a free radical initiator. Also disclosed is a cured silane-modified oil which includes the reaction product of the silane-modified oil and water. Compositions according to the disclosure have relatively low viscosities (facilitating their application to a substrate) and have relatively high levels of silane grafting (resulting in non-leaching cured compositions with a high gel content).

31 Claims, 5 Drawing Sheets

MOISTURE CURABLE OIL AND FAT COMPOSITIONS AND PROCESSES FOR PREPARING THE SAME

BACKGROUND OF THE DISCLOSURE

1. Field of the Disclosure

Processes for modifying naturally occurring oils and fats with reactive silyl groups that cure simply upon exposure to moisture and related compositions are disclosed. Such compositions are produced by heating the oil and an unsaturated hydrolysable silane in the presence of a catalyst under inert atmosphere to graft the hydrolysable silyl group to the oil.

2. Brief Description of Related Technology

The use of renewable resources feedstock as an alternative to petroleum-based materials is desirable and advantageous as it will decrease the dependency on dwindling crude oil reserves and can reduce the danger of global warming. It is well known that natural oils and fats have been used as important components, especially as drying oils, in alkyd and similar resins. The cured coatings obtained from such drying oils have been noted for their anticorrosion properties, excellent water barrier, enhanced chemical protection, and high wear and UV resistant. These coatings are said to be durable under extreme weather conditions while also providing aesthetically pleasing luster finishes. The "drying" ability of these oil compositions is achieved by air oxidation when the unsaturation sites of the fatty acids undergo crosslinking upon exposure to oxygen. The presence of trace amounts of certain metal salts, such as cobalt naphtheneate, was usually added as a catalyst to attain sufficiently rapid cure times. Thus, such curable oils must include linseed oil or a drying oil having drying properties generally similar to linseed oil in sufficient amounts to yield said useful compositions. However, linseed oil and similar drying oils, which are derived from multitude of unsaturated fatty esters in their triglyceride structure are relatively expensive and are not commonly available. Further, the oxidation reaction that leads to drying and curing of these oils is highly exothermic and care must be exercised to prevent fire hazards when working with these oils. In practice, many compositions that include linseed oil and the like must be diluted in a volatile organic solvent, which would evaporate into the atmosphere upon application and would contribute to air pollution. Alternatively, the oil was dispersed in water, instead of dissolving it in organic solvents, however, such suspensions required the use of surfactant stabilizing agents, which remained in the finished coating and degraded from its physical properties and its aesthetic appearance as described in details in T. Nabuurs et al., *Prog. in Org. Coating* 27, 163 (1996). It is therefore desirable to have curable compositions derived from common and readily available fats and natural oils that will cure in a single stage upon exposing them to the atmosphere without all the deficiencies of the air oxidation oils.

Much effort has been directed to modify the structure of common fats and oils to yield specific reactive sites that could be crosslinked and therefore function as a drying oil. Examples include formation of epoxides, hydroxyls, aldehydes and grafting of polymers as reviewed by Biermann et al. in *Angew. Chem. Int. Ed.* 39, 2206 (2000). However, this approach requires either activation of the cure system by applying heat or initiating the cure by mixing the oil with an initiator that is stored in a separate compartment from the oil.

There are many patents related to silicone sealants that are based upon the use of alkoxy functional polysiloxanes and alkoxy functional crosslinkers. Representative of the prior art is U.S. Pat. No. 3,334,067 to Weyenberg. This patent discloses a method of making one component room temperature siloxane rubber whereby the compositions are stable in the absence of moisture, but cure upon exposure to moisture. The method comprises mixing in the absence of moisture a hydroxyl end-blocked siloxane polymer with an alkoxy silane of the formula $R'Si(OR'')_3$. Similarly, U.S. Pat. No. 3,383,355 to Cooper discloses polysiloxanes having alkoxy groups bonded to terminal silicon atoms. These functional diorganopolysiloxanes having from two to three alkoxy groups attached to each terminal silicon atom are curable in the presence of moisture and a suitable hydrolysis and condensation catalyst to yield a rubbery material. U.S. Pat. No. 3,856,839 to Smith et al. also discloses the cure of a composition containing methyltrimethoxysilane and a silanol terminated polydiorganosiloxane fluid. However, none of the teachings related to the incorporation of the reactive silanes to polyorganosilicon to produce compositions that will cure by moisture can be used to attach the reactive silanes to natural fat and oils. This is the case since it is not possible to attach the moisture sensitive reactive silanes by condensation or hydrosilylation to natural oils and fats as has been taught in the prior art.

There are only a few examples where reactive silanes were attached to natural oils and fats; U.S. Pat. No. 3,424,598 to Snyder et al. discloses the reaction of trichlorosilane with beef tallow, soybean oils or fatty substances esters of trihydric alcohol containing unsaturated acyl groups to prepare water repellent surface coatings for concrete. Accordingly, the trichlorosilane was initially reacted with the oil under nitrogen bubbling in ether and then irradiated for 48 hours at 35° C. with Hg lamps. Upon removing the solvent and excess chlorosilane, a syrupy colorless liquid was obtained. It is claimed that such products when applied to cured concrete reduced the water absorbance of the concrete, provided good weather resistance (including freezing and thawing) and showed excellent resistance to microbial degradation. It is apparent to these expert in the art that this method of UV catalyzed hydrosilylation is limited only to chlorosilanes and will not proceed to any significance with other silanes if the double bonds are not in the terminal position. Furthermore, the use of chlorosilanes is not desirable since the by-product of the moisture activated cure is strongly acidic HCl, which will cause saponification of the triglycerides. The presence of HCl is further undesirable as it can lead to corrosion of any metallic substrates or substrates that contain metals (as in reinforced concrete).

U.S. Pat. No. 2,735,825 to Kress discloses silicone-modified alkyd coating having superior weather and chemical resistance and good curability that were obtained by reacting oil-modified alkyds with acid hydrolysis products of chlorosilanes and then diluted in a solvent. Similarly, U.S. Pat. No. 2,717,900 to Plueddemann and BE Pat. No. 510,419 issued Aug. 1, 1952 to Goneberg disclose silicones containing oils that were prepared by the reaction of polyhydric alcohols with mono- or diglycerides of fatty acids and a silanol. Such compositions are derived by attaching the silicon group via a Si—O—C linkage. However, these compositions and similar examples in the prior art of mixtures of various silanes and natural oils, although said to be "curing", are not capable of crosslinking via hydrolytically stable covalent bonds to a network and the so called "cure" is not activated by atmospheric moisture.

Another approach is disclosed in U.S. Pat. No. 4,512,926 to Kampf which discloses a process for the silylation of unsaturated, naturally occurring oils by reacting them with appropriate silanes at 200° C.-350° C. under an inert gas and in the absence of a catalyst/initiator. The products of this invention are claimed to be useful for soil stabilization, or additives to improve the properties of adhesives, cements, sealing and caulking compounds or as dispersion agents for pigments. Additionally, they can be used to render substrates, such as paper, textile materials, wood, cardboard, and building materials, hydrophobic. The teaching of Kampf, however, produces poor network gels where a substantial amount of the oil molecules remains unreacted and uncurable. Thus, upon exposure to moisture, substantial fraction of the composition remains liquid that tends to migrate out of the bulk and to stain the substrate surface and the surrounding areas.

Objects

A more convenient approach would be a single compartment system where all the components are stored together and the cure is activated by exposing the formulation to atmospheric moisture at ambient conditions such as in compositions containing reactive silicones. The moisture-activated cure chemistry is based on hydrolysis of organic groups attached to a silicon atom through hydrolytically unstable covalent bonds such as in alkoxy silanes. Upon hydrolysis of the alkoxy groups by atmospheric moisture, silanol groups are formed, which are then condensed to yield stable crosslinked siloxane bonds. Further, it would be desirable to provide a curable oil that has a relatively low viscosity (i.e., so that it can be conveniently applied to a substrate) and that exhibits limited or no leaching upon cure.

These and other objects may become increasing apparent by reference to the following description and the drawings.

SUMMARY

Processes for modifying naturally occurring oils and fats with reactive silyl groups that cure simply upon exposure to moisture and related compositions are disclosed. Such compositions are produced by heating the oil and an unsaturated hydrolysable silane in the presence of a catalyst under an inert atmosphere to graft the reactive silyl groups to the oil. A cured composition according to the disclosure includes stable siloxane crosslinks that are obtained when the reactive silyl groups are hydrolyzed and subsequently condensed to form a gel network of covalent siloxane linkages. Thus, the expression "drying" or "curing" herein does not mean simple hardening as a result of baking at elevated temperatures or oxidizing and degradation of the double bonds, but rather covalent network formation due to silanol formation and condensation.

In an embodiment, a moisture-curable, silane-modified oil comprises: (a) an unsaturated oil comprising at least one unsaturated aliphatic hydrocarbon chain per molecule of the unsaturated oil, and (b) a hydrolysable silyl group (e.g., methoxy silyl groups, ethoxy silyl groups, acetoxy silyl groups) grafted to the unsaturated aliphatic hydrocarbon chain. The silane-modified oil has a degree of unsaturation that is substantially similar that of the unsaturated oil (e.g., the degree of unsaturation of the silane-modified oil is at least about 70%, at least about 80%, at least about 90%, or at least about 95% of that of the unsaturated oil). Preferably, the hydrolysable silyl group is represented by Formula II:

$$—SiR''_m R_{3-(n+m)} X_n \qquad \text{[Formula II]}$$

In Formula II, (i) X is a hydrolysable functional group selected from the group consisting of alkoxy groups, aryloxy groups, carboxyloxy groups, halogens, and combinations thereof (preferably methoxy, ethoxy, and/or acetoxy); (ii) R is selected from the group consisting of hydrogen, saturated aliphatic hydrocarbon groups, saturated alicyclic hydrocarbon groups, aryl hydrocarbon groups, heterocyclic hydrocarbon groups, and combinations thereof, the hydrocarbon groups containing from 1 to 30 (e.g., 1-10, 1-6) carbon atoms; (iii) R" is selected from the group consisting of an unsaturated hydrocarbon residue containing from 2 to 30 (e.g., 2-14, 2-6) carbon atoms, a graft reaction product thereof, and combinations thereof; and (iv) n ranges from 1 to 3 (preferably 3), m ranges from 0 to 2, and n+m≦3. Preferably, substantially all of the unsaturated oil molecules have at least one hydrolysable silyl group grafted thereto via the unsaturated aliphatic hydrocarbon chain; for example, the molar ratio of grafted hydrolysable silyl groups to unsaturated oil molecules can range from about 1.2 to about 5 (e.g., 1.4-3, 1.6-2.5).

In another embodiment, any of the foregoing moisture-curable, silane-modified oils can be provided in a mixture with a curing catalyst (e.g., a titanium catalyst, a tin catalyst, and combinations thereof).

Also disclosed is a cured silane-modified oil composition. The cured composition comprises: a networked gel polymer of any of the foregoing silane-modified oils, wherein the silane-modified oil molecules are covalently crosslinked to at least one other silane-modified oil molecule via covalent intermolecular siloxane crosslinks derived from hydrolyzed and condensed hydrolysable silyl groups.

In another embodiment, a cured silane-modified oil comprises the reaction product of: (a) any of the foregoing moisture-curable, silane-modified oils; and (b) water. Further, (i) at least some of the hydrolysable silyl groups of the silane-modified oil have been hydrolyzed with the water and condensed, thereby forming covalent intermolecular siloxane crosslinks between silane-modified oil molecules in the cured silane-modified oil; and (ii) the cured silane-modified oil is sufficiently crosslinked with the intermolecular siloxane crosslinks to form a networked gel. The intermolecular siloxane crosslinks preferably are represented by Formula III:

$$—R'''—Si(Y)_2—O—Si(Y)_2—R'''— \qquad \text{[Formula III]}$$

In Formula III, (i) the Y moieties are independently selected from the group consisting of —OH, —R, —R", —O—Si(Y)$_2$—R'''—, and combinations thereof; (ii) the R''' moieties are independently selected from the group consisting of hydrocarbon residues ranging from 2 to 30 (e.g., 2-14, 2-6) carbon atoms; (iii) R is selected from the group consisting of hydrogen, saturated aliphatic hydrocarbon groups, saturated alicyclic hydrocarbon groups, aryl hydrocarbon groups, heterocyclic hydrocarbon groups, and combinations thereof, the hydrocarbon groups containing from 1 to 30 (e.g., 1-10, 1-6) carbon atoms; and (iv) R" is selected from the group consisting of an unsaturated hydrocarbon residue containing from 2 to 30 (e.g., 2-14, 2-6) carbon atoms, a graft reaction product thereof, and combinations thereof. In a further refinement, (i) the unsaturated oil comprises soybean oil; (ii) the Y moieties are independently selected from the group consisting of —OH, —O—Si(Y)$_2$—R'''—, and combinations thereof; and (iii) the R''' moieties are independently selected from the group consisting of —CH$_2$CH$_2$—, —CH$_2$CH$_2$CH$_2$—, and combinations thereof. Preferably, substantially all of the unsaturated oil molecules are crosslinked to at least one other unsaturated oil molecule via the intermolecular siloxane crosslinks.

Also disclosed is a process for forming a moisture-curable, silane-modified oil. The process comprises: reacting an unsaturated oil with an unsaturated hydrolysable silane in the presence of a free radical initiator to form a silane-modified oil comprising hydrolysable silyl groups grafted to the unsaturated oil. Preferably, the unsaturated hydrolysable silane comprises a compound according to Formula I:

$$R''_m SiR_{4-(n+m)} X_n \qquad \text{[Formula I]}$$

In Formula I, (i) X is a hydrolysable functional group selected from the group consisting of alkoxy groups, aryloxy groups, carboxyloxy groups, halogens, and combinations thereof (preferably methoxy, ethoxy, and/or acetoxy); (ii) R is selected from the group consisting of hydrogen, saturated aliphatic hydrocarbon groups, saturated alicyclic hydrocarbon groups, aryl hydrocarbon groups, heterocyclic hydrocarbon groups, and combinations thereof, the hydrocarbon groups containing from 1 to 30 (e.g., 1-10, 1-6) carbon atoms (e.g., methyl, ethyl, and/or fluoropropyl); (iii) R" is an unsaturated hydrocarbon residue containing from 2 to 30 (e.g., 2-14, 2-6) carbon atoms; and, (iv) n ranges from 1 to 3 (preferably 3), m ranges from 1 to 3, and n+m≦4. In a further refinement, R" is $CH_2=CH-R'-$ and R' is a hydrocarbon residue containing from 0 to 12 carbon atoms (e.g., R" is vinyl and/or allyl). The unsaturated hydrolysable silane can be polyunsaturated (e.g., m is or 3, and/or R" is polyunsaturated). In an embodiment, R" is an aryl unsaturated hydrocarbon residue (e.g., $CH_2=CH-Ph-$). Suitable unsaturated hydrolysable silanes include vinyltrimethoxysilane, vinyltriethoxysilane, vinyltriacetoxysilane, allyldimethylacetoxysilane, allyltriisopropoxysilane, and/or allylphenyidiphenoxysilane. Suitable free radical initiators include a thermal peroxide initiator selected from the group consisting of benzoyl peroxide, di-t-butylperoxide, 2,5-dimethyl-2,5-di(t-butylperoxide)hexane, bis(methylbenzoyl)peroxide, bis(dimethylbenzoyl)peroxide, dicumylperoxide, t-butyl 3-isopropenylcumyl peroxide, butyl 4,4-bis(tert-butylperoxy)valerate, and/or bis(trimethylbenzoyl)peroxide. Preferred reaction conditions include reacting the unsaturated oil with the unsaturated hydrolysable silane in the presence of the free radical initiator at a temperature ranging from about 100° C. to about 350° C. (e.g., 100° C.-180° C., 200° C.-300° C.) under an inert atmosphere that is substantially free from water, for example where the weight ratio of the free radical initiator to the unsaturated oil ranges from about 0.001 to about 0.1 (e.g., 0.002-0.05, 0.005-0.02). Any excess, unreacted unsaturated hydrolysable silane from the silane-modified oil can be removed (e.g., by heating or other distillation methods).

Also disclosed is a moisture-curable, silane-modified oil produced according to any of the foregoing processes.

Another disclosed process for curing a silane-modified oil includes: providing any of the foregoing silane-modified oils, and curing the silane-modified oil with water, thereby hydrolyzing and condensing the hydrolysable silyl groups to form covalent intermolecular siloxane crosslinks in the silane-modified oil. In a refinement, the silane-modified oil is applied to a substrate (e.g., glass, wood, paper, cement, metal, polymer) prior to curing. Preferably, a curing catalyst (e.g., titanium catalyst, tin catalyst; for example provided as a mixture with the silane-modified oil) is additionally provided to the silane-modified oil and the water, thereby accelerating the rate of intermolecular crosslink formation. Prior to curing, the weight ratio of the curing catalyst to the silane-modified oil preferably ranges from about 0.002 to about 0.06 (e.g., 0.005-0.03). The curing water is preferably atmospheric moisture (e.g., up to about 5 vol. % water in air, 0.5 vol. %-5 vol. %, or 1 vol. %-2 vol. %).

Also disclosed is a cured silane-modified oil produced according to any of the foregoing processes.

In any of the foregoing compositions and/or processes, the unsaturated oil can comprise a triglyceride derived from one or more of soybean oil, safflower oil, linseed oil, corn oil, olive oil, sunflower oil, canola oil, sesame oil, cottonseed oil, palm oil, poppy-seed oil, peanut oil, coconut oil, rapeseed oil, tung oil, castor oil, fish oil, and whale oil. Alternatively or additionally, the unsaturated oil can comprise one or more unsaturated fatty acids having from 10 to 24 carbon atoms, esters thereof, monoglycerides thereof, diglycerides thereof, and combinations thereof. Similarly, suitable curing catalysts can be selected from the group consisting of titanium naphthenate, tetraisopropyltitanate, tetrabutyltitanate, bis(acetylacetonyl)-diisopropyltitanate, tetra-2-ethylhexyl-titanate, tetraphenyltitanate, triethanolaminetitanate, organosiloxytitanium compounds, beta-dicarbonyl titanium compounds, dibutyl tin dilaurate, dibutyl tin diacetate, dioctyl tin dilaurate, tin octanoate, and combinations thereof. In various embodiments, the silane-modified oil has a gel content of at least about 70% (e.g., 80%, 90%, 95%) once cured, the silane-modified oil has a viscosity that is about 180% or less (e.g., 160%, 140%, 120%, 110%) of that of the unsaturated oil, and/or the silane-modified oil has an iodine number that is at least about 80% (e.g., 90%, 95%) of that of the unsaturated oil.

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1:
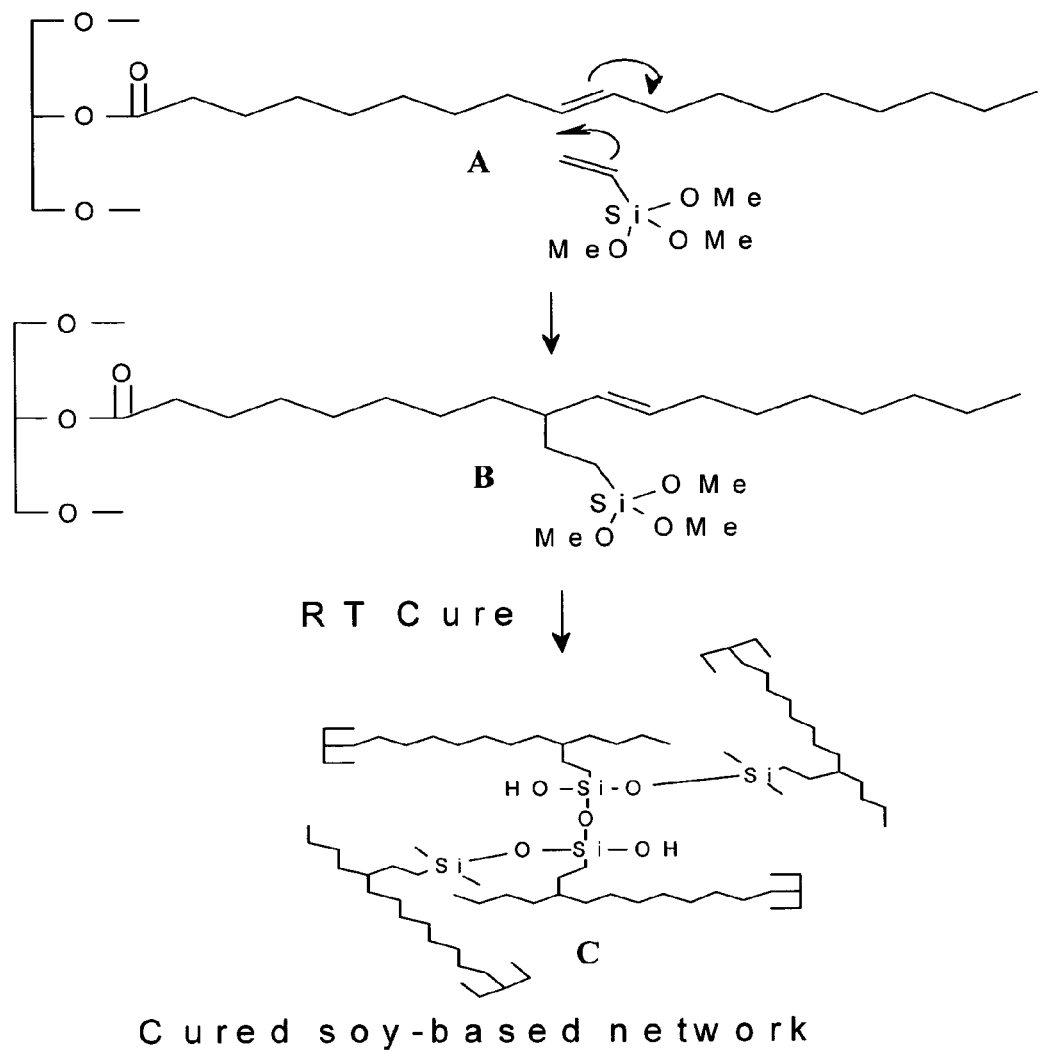
FIG. 1 illustrates grafting and curing reactions associated with an unsaturated triglyceride oil and unsaturated hydrolysable silane.

While the disclosed compositions and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

A moisture-curable, silane-modified oil according to the disclosure includes (a) an unsaturated oil having at least one unsaturated aliphatic hydrocarbon chain per molecule of the unsaturated oil, and (b) at least one hydrolysable silyl group grafted to the unsaturated aliphatic hydrocarbon chain. The hydrolysable silyl group is generally grafted to the unsaturated aliphatic hydrocarbon chain at an internal carbon position along the length of the chain, and not at a terminal carbon (i.e., a carbon at the chain end opposing an ester/acid group in the fatty acid/triglyceride). The silane-modified oil has a degree of unsaturation that is substantially similar that of the unsaturated oil. In an embodiment, the silane-modified oil can be provided in a mixture with a curing catalyst (e.g., titanium catalyst, tin catalyst). Also disclosed is a cured silane-modified oil which includes the reaction product of the silane-modified oil and water. In the cured oil, at least some of the hydrolysable silyl groups of the silane-modified oil have been hydrolyzed with the water (i.e., to form silanols) and subsequently condensed, thus forming covalent intermolecular siloxane crosslinks between silane-modified oil molecules in the cured oil. As a result, the cured silane-modified oil is sufficiently crosslinked with the intermolecular siloxane crosslinks to form a networked gel.

A process for forming the moisture-curable, silane-modified oil according to the disclosure includes reacting the unsaturated oil with an unsaturated hydrolysable silane in the presence of a free radical initiator. The reaction thus forms a silane-modified oil having hydrolysable silyl groups grafted to the unsaturated oil molecules (e.g., at least one grafted hydrolysable silyl group per unsaturated oil molecule). Also disclosed is a process for curing the silane-modified oil. The process includes curing the silane-modified oil with water, thereby hydrolyzing and condensing the hydrolysable silyl groups to form covalent intermolecular siloxane crosslinks in the silane-modified oil.

The unsaturated oil can be derived from triglycerides composed of fatty acid ester groups that collectively comprise at least one site of alkenyl unsaturation (e.g., at least one unsaturated aliphatic hydrocarbon chain per molecule of unsaturated oil; generally not including silicone oils, alkoxy-terminated (or other hydrolysable group-terminated) silicone oils, or terminal hydrosilated oils). For example, a particular triglyceride molecule can have three aliphatic fatty acid ester groups, at least one of which has at least one unsaturated carbon-carbon double bond. Mono- and di-glycerides also can be used when there is sufficient unsaturation in the fatty acid esters. The unsaturated oil generally includes natural oils, for example any unsaturated vegetable or animal oils or fats; more specifically, the term "oil" generally refers to lipid structures (natural or synthetic), regardless of whether they are generally liquid at room temperature (i.e., oils) or solid at room temperature (i.e., fats). Examples of unsaturated oils include, but are not limited to, natural oils such as soybean oil (preferred), safflower oil, linseed oil, corn oil, sunflower oil, olive oil, canola oil, sesame oil, cottonseed oil, palm oil, poppy-seed oil, peanut oil, coconut oil, rapeseed oil, tung oil, castor oil, fish oil, whale oil, or any mixture thereof. Additionally, any partially hydrogenated vegetable oils or genetically modified vegetable oils can also be used. Examples of partially hydrogenated vegetable oils or genetically modified vegetable oils include, but are not limited to, high oleic safflower oil, high oleic soybean oil, high oleic peanut oil, high oleic sunflower oil and high erucic rapeseed oil (crambe oil). Alternatively or additionally, any unsaturated fatty acids (e.g., containing 10 to 24 carbons or 12 to 20 carbons in the unsaturated aliphatic hydrocarbon chain) or esters thereof (e.g., alkyl esters, hydrocarbon esters containing from 1 to 12 carbon atoms), either individually or as mixtures, also can be used as an unsaturated oil according to the disclosure. The iodine values of the unsaturated oils preferably range from about 40 to 240 (e.g., about 80 to 240, about 120 to 160). When oils having lower iodine values are used, lower concentrations of hydrolysable silyl groups will be obtained in the silane-modified oil.

The unsaturated hydrolysable silane includes a silicon-based compound having an unsaturated hydrocarbon residue and at least one hydrolysable functional group bonded to a silicon atom. An example of a suitable unsaturated hydrolysable silane is represented by Formula I:

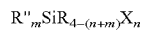  [Formula I]

In Formula 1, (i) X is a hydrolysable functional group, (ii) R is a terminal group or atom, (iii) R" is an unsaturated hydrocarbon residue, and (iv) n is an integer ranging from 1 to 3, m is an integer ranging from 1 to 3, and n+m≦4. The value of n is preferably 2 or 3 (more preferably 3), thereby permitting more than one siloxane linkage in the cured silane-modified oil and facilitating the formation of networked gel polymer. Generally, the unsaturated hydrolysable silane contains a single carbon-carbon unsaturation (i.e., m is 1) so that the silane is grafted to the unsaturated oil without any undesired crosslinking between unsaturated oil molecules. In some embodiments, however, the unsaturated hydrolysable silane is polyunsaturated (e.g., m is 2 or 3 and/or R" is polyunsaturated). Preferred unsaturated hydrolysable silanes include vinyltrimethoxysilane, vinyltriethoxysilane, vinyltriacetoxysilane, allyldimethylacetoxysilane, allyltriisopropoxysilane, and allylphenyldiphenoxysilane. R", R, and X can be chosen independently from of each other, and specific examples of the various groups are given below.

Examples of hydrolysable functional groups X include alkoxy (e.g., methoxy, ethoxy), carboxyloxy (e.g., acetoxy), or aryloxy groups. Optionally, X can be a halogen such as chloride or bromide, although the halogens are less preferred as they lead to formation of strong acids upon hydrolysis, which acids are preferably neutralized to prevent saponification of any fatty acid esters in the oil (e.g., triglyceride ester bonds). Thus, in some embodiments, the hydrolysable functional groups (or hydrolysable silyl groups) do not include halogens. Most preferably, X is either a methoxy and/or acetoxy group. Such silanes are commonly available and their methods of manufacture are well known. Preferred are the silanes in which there are three hydrolysable groups present, such as vinyltrimethoxysilane or vinyltriacetoxysilane.

The terminal group R is preferably a hydrogen, a saturated hydrocarbon group, a saturated alicyclic hydrocarbon group, an aryl hydrocarbon group, a heterocyclic hydrocarbon group, or a combination thereof. The hydrocarbon groups generally containing from 1 to 30 carbon atoms (e.g., 1 to 10 carbon atoms, 1 to 6 carbon atoms). For example, R can be a hydrogen, a saturated alkyl hydrocarbon group, a substituted saturated alkyl hydrocarbon group, an aryl group, or a substituted aryl group. Alkyl groups can be any hydrocarbon including carbon atoms in either a linear or a branched configuration. Alkyl/aryl groups could be hydrocarbons or substituted hydrocarbons where the substitution includes heteroatoms, halogens, ethers, aldehydes, ketones, and the like. Preferred alkyl groups are methyl, ethyl, and fluoropropyl groups. In a preferred embodiment, however, n is 3, m is 1, and the terminal group R is not present in the unsaturated hydrolysable silane.

The unsaturated hydrocarbon residue R" preferably contains from 2 to 30 carbon atoms (e.g., 2 to 14 carbon atoms, 2 to 6 carbon atoms). Generally, unsaturated hydrocarbon residue R" is monounsaturated; however, R" can be polyunsaturated (e.g., a dienyl group). In an embodiment, the unsaturated functionality of R" is at a terminal end of R" (i.e., R" is $CH_2=CH-R'-$ where R' is a hydrocarbon residue containing from 0 to 12 carbon atoms) to facilitate the grafting of the unsaturated hydrolysable silane to the unsaturated oil. The hydrocarbon residues preferably include alkyl, substituted alkyl, aryl, or substituted aryl segments such as methyl, ethyl, propyl, and phenyl (e.g., $CH_2=CH-Ph-$). Most preferably, R" is either a vinyl ($CH_2=CH-$) or allyl ($CH_2=CH-CH_2-$) group.

The relative amounts of the unsaturated oil and the unsaturated hydrolysable silane amounts are adjusted according to the specific grafting reaction conditions (e.g., temperature, reaction time, free radical initiator). Preferably, prior to the grafting reaction, the unsaturated hydrolysable silane is present in a molar excess relative to the unsaturated oil, for example with the molar ratio of the unsaturated hydrolysable silane to the unsaturated oil ranging from about 1 to about 20, about 2 to about 10, about 3 to about 8, or about 4 to about 6. It is desirable to have at least 1 mole of reactive silyl groups (i.e., the reactive, hydrolysable silane group grafted to the unsaturated oil) per molecule of the unsaturated oil (e.g., fatty acid triglycerides) to ensure complete cure at or above the gel point. More specifically, the molar ratio of grafted hydrolysable silyl groups to unsaturated oil molecules ranges from about 1.2 to about 5 (e.g., about 1.4 to about 3 or about 1.6 to about 2.5). Under these conditions, minimum amounts of uncured unsaturated oil will be left in the composition after cure (i.e., either (1) unsaturated oil molecules not containing a hydrolysable silyl group or (2) unsaturated oil molecules containing a hydrolysable silyl group that did not hydrolyze/ condense to form a siloxane crosslink with another hydrolysable silyl group). If, however, insufficient amounts of the unsaturated hydrolysable silane are used, a portion of the unsaturated oil will not be crosslinked into the gel network and will remain free, tending to leach/bleed from a cured composition. Preferably, after the grafting reaction, substantially all of the unsaturated oil molecules have at least one hydrolysable silyl group grafted thereto via the unsaturated aliphatic hydrocarbon chain; thus, substantially no uncured unsaturated oil is present in a cured composition and/or able to leach from the cured composition. For example, uncured/ leachable oil is preferably about 5 wt. % or less (e.g., about 2 wt. %, 1 wt. %, or 0.1 wt. % or less), relative to the initial amount of unsaturated oil. In many applications, such incomplete cure is undesirable and may lead to problems related to staining of areas surrounding the point(s) of application, poor performance and problems related to adhesion, water resistance, and/or aesthetic appearance. Accordingly, a level of uncured unsaturated oil present in a post-grafting sample is preferably small enough to minimize such adverse properties.

The free radical initiator assists in the grafting reaction of the unsaturated hydrolysable silane onto the unsaturated oil (e.g., via the unsaturated aliphatic chain of the unsaturated oil molecule). Any free radical initiator generally known in the art is appropriate, with thermal initiators that generate free radicals upon heating being preferred. Examples include, but are not limited to, organic peroxides, such as a benzoyl peroxide, di-t-butylperoxide, 2,5-dimethyl-2,5-di(t-butylperoxide)hexane, bis-(o-methylbenzoyl)peroxide, bis(m-methylbenzoyl)peroxide, bis(p-methylbenzoyl)peroxide, or similar monomethylbenzoyl peroxides, bis(2,4-dimethylbenzoyl) peroxide, or a similar dimethylbenzoyl peroxide, dicumylperoxide, t-butyl 3-isopropenylcumyl peroxide, butyl 4,4-bis (tert-butylperoxy)valerate, bis(2,4,6-trimethylbenzoyl) peroxide, or a similar trimethylbenzoyl peroxide. The free radical initiator leads to higher portions of the reactive hydrolysable silyl group grafted to the unsaturated oil and minimizes the risk of having an incomplete network upon curing that permits free (i.e., non-crosslinked) unsaturated oil molecules to diffuse out of the bulk. Such diffusion of unreacted unsaturated oil molecules from the network has adverse effects on the physical properties of the gel network itself as well as the surrounding areas. The initiator is added in any appropriate amount to ensure that the resulting composition will cure by grafting sufficient hydrolysable silyl groups onto the unsaturated oil. Preferably the initiator is used in an amount of about 0.1 wt. % to about 10 wt. % (e.g., about 0.2 wt. % to about 5 wt. % or about 0.5 wt. % to about 2 wt. %), relative to the weight of the unsaturated oil component.

Preferably, the free radical initiator is used in a reaction mixture that is either substantially free of or free of antioxidants and/or peroxide scavengers. In some cases, antioxidants and/or peroxide scavengers (e.g., t-butyl pyrocatechol, butylated hydroxy toluene, butylated hydroxy anisole, hydroquinone) are added to unsaturated silanes to prevent the spontaneous polymerization of the unsaturated silanes. However, the use of the free radical initiator without the antioxidant/peroxide scavenger promotes the silylation graft reaction while also reducing the rate of undesirable side reactions. Further, spontaneous polymerization of the unsaturated silanes was not observed in the various Example formulations prepared and analyzed.

A suitable process for performing the graft reaction to form the water-curable, silane-modified oil includes preparing a reaction mixture that includes about 1 mole of unsaturated oil per 5 moles of the unsaturated hydrolysable silane and about 1 wt. % peroxide initiator (relative to the unsaturated oil) in a closed flask under an inert (e.g., nitrogen) atmosphere. The reaction mixture should be substantially water-free to prevent premature hydrolysis and/or siloxane crosslinking (e.g., sufficiently free of water to prevent reaction based time available for reaction, ambient temperature, pH, etc.). For example, the reaction mixture is pumped under a nitrogen blanket into a 2 L Parr reactor that has been purged with dry nitrogen for about 5 minutes to ensure dry atmosphere. The Parr reactor (from Parr Instrument Company, Moline, Ill., USA) is equipped with a mechanical stirrer, a sampling port and thermocouple well. The temperature of the reactor is then adjusted using an external controller and the mixture is heated while stirring at 200 rpm in order to mix the reactants and distribute the heat uniformly throughout the reactor. Typical reaction temperatures are between about 100° C. to about 350° C. For common vinyl and allyl unsaturated hydrolysable silanes, the reaction temperature is generally in the higher end of the range, (e.g., about 200° C. to about 350° C., or about 200° C. to about 300° C. When the unsaturated hydrocarbon residue R" is an aryl residue (e.g., $CH_2=CH-Ph-$), however, lower reaction temperatures may be suitable (e.g., about 100° C. to about 200° C., or about 100° C. to about 180° C.). Since many of the unsaturated hydrolysable silanes have boiling points below the reaction temperature, care is taken to ensure that the reactor can withstand the pressure build-up during the reaction. At the end of the reaction, the heat is turned off, allowing the silane-modified oil to cool down to room temperature. Excess unreacted unsaturated hydrolysable silane can then be removed from the product by simple evaporation or be left in the product. The amount of reacted (i.e., grafted) and unreacted hydrolysable silane in the oil is determined by placing a sample in a thermo-gravimetric analyzer (TGA) held at 160° C. for a period of about 20-30 minutes. Any unreacted hydrolysable silane is volatilized away from the product, registering as a weight loss in the TGA. The concentration of the grafted silane is calculated by subtracting the weight loss of the volatile fraction (i.e., unreacted silane) from the initial weight of unsaturated hydrolysable silane in the reaction mixture.

The moisture-curable, silane-modified oil product has a degree of unsaturation that is substantially similar that of the unsaturated oil. Preferably, the degree of unsaturation of the silane-modified oil is at least about 70% (e.g., at least about 80%, at least about 90%, at least about 95%, and/or up to about 100%) of that of the unsaturated oil. The similar degrees of unsaturation represent a minimization of undesirable coupling reactions between unsaturated oil carbon-carbon double bonds while promoting the grafting reaction of the unsaturated hydrolysable silane onto the unsaturated oil chains. The undesirable coupling reactions between unsaturated oil molecules (i.e., "bodying" reactions) tend to increase the molecular weight of the unsaturated oil while also reducing the available sites for unsaturated hydrolysable silane grafting. The reduction of available grafting sites further tends to result in bodied unsaturated oil molecules that, absent any hydrolysable silane functionality, will undesirably leach from a cured composition.

The degree of unsaturation can be conveniently expressed by any of a variety of methods. For example, the total number of carbon-carbon double bonds in both the original unsaturated oil and the silane-modified oil product can be determined (e.g., by NMR spectroscopy) and compared. Preferably, the silane-modified oil contains at least about 70% (e.g., at least about 80%, at least about 90%, at least about 95%, and/or up to about 100%) of the number of carbon-carbon double bonds originally present in the original unsaturated oil. For example, as illustrated in FIGS. 1A and 1B (discussed in more detail below), the unsaturated aliphatic hydrocarbon chain retains its carbon-carbon double bond, even though the position of the double bond changes as a result of the grafting reaction. Alternatively, the degree of unsaturation can be characterized by the iodine number (e.g., amount of iodine consumed by a substance, for example as determined by ASTM D1959, ASTM D5768, DIN 53241, or equivalent). Preferably, the silane-modified oil has an iodine number that is at least about 70% (e.g., at least about 80%, at least about 90%, at least about 95%, and/or up to about 100%) of the iodine number of the original unsaturated oil, thus indicating that relatively few (if any) of the carbon-carbon double bonds in the original unsaturated oil have been lost.

The relative retention of unsaturated character in the moisture-curable, silane-modified oil product also can be expressed by its viscosity, which remains similar to that of the reactant oil that was used. Preferably, the silane-modified oil has a viscosity that is about 180% or less (e.g., about 160% or less, about 140% or less, about 120% or less, or about 110% or less and/or at least about 60%, at least about 80%, or at least about 100%) of the viscosity of the original unsaturated oil, thus indicating a relatively low degree of bodying that results in increased molecular weight and viscosity. Thus, when a low viscosity vegetable oil is employed as the unsaturated oil, the similarly low viscosity of the silane-modified oil product facilitates smooth, continuous film formation when deposited as a coating. This low viscosity characteristic further allows the silane-modified oil to be brushed, dipped, sprayed, or applied onto a substrate by any common techniques using conventional equipment known in the art to form continuous aesthetic protective films. It was noted that even in the absence of adhesion promoters, excellent adhesion of the cured films was obtained on glass, wood, paper, cement, metal (specifically steel), and polymer (specifically polystyrene and polyester) surfaces. Prior to application to the substrate, the silane-modified oil can be combined with a filler (e.g., fumed silica) to act as a reinforcing agent that improves the mechanical properties of the cured oil and also to improve adhesion of the cured oil to various substrates (e.g., glass). The protective coating thus obtained acted as an excellent moisture barrier and prevented rusting when coated on untreated steel substrates subsequently exposed to moisture.

The silane-modified oil can be further characterized in terms of the particular structure of its hydrolysable silyl group(s), for example as expressed by Formula II:

$$-\mathrm{SiR''}_m\mathrm{R}_{3-(n+m)}\mathrm{X}_n \quad \text{[Formula II]}$$

In Formula II, X and R can represent the same hydrolysable functional groups and terminal groups/atoms as in Formula I. In Formula II, n ranges from 1 to 3 (preferably 3), m ranges from 0 to 2, and $n+m \leq 3$. Because the hydrolysable silyl group of Formula II is grafted to the unsaturated oil, R'' can represent both the unsaturated hydrocarbon residues of Formula I or the graft reaction product of the unsaturated hydrocarbon residues. As an example, R'' can represent the vinyl group ($CH_2=CH-$) or the ethylene graft reaction product of the vinyl group ($-CH_2CH_2-$), in the event that the unsaturated hydrolysable silane is polyunsaturated and/or grafted to more than one unsaturated aliphatic hydrocarbon chain. Generally, the hydrolysable silyl group is grafted to the unsaturated aliphatic hydrocarbon chain via a linking group R''' that represents the graft reaction product of R''. In this case, the hydrolysable silyl group that is directly grafted to the unsaturated aliphatic hydrocarbon chain (i.e., via the linking group R''') can be represented by Formula IIa:

$$-\mathrm{R'''SiR''}_m\mathrm{R}_{3-(n+m)}\mathrm{X}_n \quad \text{[Formula IIa]}$$

The silane-modified oil can then be cured by exposing it to water, thereby hydrolyzing the hydrolysable silyl groups to silanol groups and subsequently condensing the silanol groups to form covalent intermolecular siloxane crosslinks in the silane-modified oil. Preferably, the curing water simply represents atmospheric moisture (e.g., up to about 5 vol. % water in air, about 0.5 vol. % to about 5 vol. %, about 1 vol. % to about 2 vol. %, alternatively about 20% to about 100% relative humidity). Thus, the silane-modified oil is simply applied to a substrate that is exposed to the atmosphere, and the silane-modified oil cures gradually as the atmospheric moisture hydrolyzes the hydrolysable silyl groups. The rate of cure depends on the concentration of the hydrolysable silyl groups, the relative humidity, the temperature, and the layer thickness of the silane-modified oil applied to a substrate. The curing temperature can be ambient temperature (e.g., about 25° C.). Alternatively or additionally, the silane-modified oil can be maintained at or otherwise heated to a controlled temperature, for example up to about 80° C. or about 25° C. to about 60° C.

The rate of cure can further be accelerated using curing catalysts known to accelerate moisture-induced reactions of hydrolysable silanes (generally known in the art as "accelerators"). Examples of suitable catalysts include titanium catalysts such as titanium naphthenate, tetrabutyltitanate, tetraisopropyltitanate, bis-(acetylacetonyl)-diisopropyltitanate, tetra-2-ethylhexyl-titanate, tetraphenyltitanate, triethanolaminetitanate, organosiloxytitanium compounds (such as those described in U.S. Pat. No. 3,294,739), and beta-dicarbonyl titanium compounds (such as those described in U.S. Pat. No. 3,334,067), both patents being herein incorporated by reference to show titanium catalysts. Alternatively, an organometallic tin condensation cure catalyst can be used to accelerate the rate of cure. Examples of tin carboxylate condensation cure catalysts include dibutyl tin dilaurate, dibutyl tin diacetate, dioctyl tin dilaurate, tin octoate, or mixtures thereof. Preferred catalysts include tetrabutyltitanate, tetraisopropyltitanate, and bis-(acetylacetonyl)-diisopropyltitanate. The amount of curing catalyst preferably ranges from about 0.2 wt. % to about 6 wt. % (e,g, about 0.5 wt. % to about 3 wt. %) relative to the weight of the silane-modified oil. When present, the curing catalyst is preferably provided as a mixture with the moisture-curable silane-modified oil so that the two components can be applied to a surface in a single operation.

The cured silane-modified oil can be further characterized in terms of the particular structure of its covalent intermolecular siloxane crosslinks, for example as expressed by Formula III:

   [Formula III]

In Formula III, the Y moieties can independently represent —OH (i.e., a hydrolyzed but uncondensed silanol), —R, —R", —O—Si(Y)$_2$—R'"—, and combinations thereof. The recursive definition of Y indicates that the siloxane crosslinks can be branched and need not be a 2-silicon crosslink (e.g., as illustrated in FIG. 1C, described in more detail below). The R moieties can represent the same terminal groups/atoms as in Formula 1, and the R" moieties can represent the same unsaturated hydrocarbon residues and graft reaction products thereof as in Formula II. The R'" moieties represent the same linking groups as in Formula II, thus generally representing a hydrocarbon residue having from 2 to 30 carbon atoms (e.g., 2 to 14 carbon atoms or 2 to 6 carbon atoms). Specifically, the R'" moieties are the linking groups grafted to the oil's unsaturated aliphatic hydrocarbon chains at both ends of the intermolecular siloxane crosslinks, thus covalently linking at least two silane-modified oil molecules together. In an embodiment of the cured oil, (i) the unsaturated oil includes soybean oil; (ii) the Y moieties independently represent —OH, —O—Si(Y)$_2$—R'"—, and combinations thereof; and (iii) the R'" moieties independently represent —CH$_2$CH$_2$—, —CH$_2$CH$_2$CH$_2$—, and combinations thereof.

In the cured silane-modified oil, substantially all of the unsaturated oil molecules are crosslinked to at least one other unsaturated oil molecule via the intermolecular siloxane crosslinks. Additionally, the leaching of non-silylated unsaturated oil molecules is limited. Once cured, the silane-modified oil preferably has a gel content of at least about 70% (e.g., at least about 80%, at least about 90%, at least about 95%, or at least about 98%). The gel content of a cured oil can be determined by equilibrating a sample of the cured oil in a solvent (e.g., about 1 g to 2 g cured oil per 50 ml of solvent, or 2 g cured oil in 50 ml of solvent) for several hours. The solvent (along with any extracted/dissolved portion of the cured oil) is then removed from the sample and dried to constant weight. The fraction of the cured oil that is not extracted is the gel fraction. Suitable solvents include toluene and chloroform, although both give similar results. The gel fraction of an uncured silane-modified oil can be determined by first curing the uncured sample according to a standard procedure. A sample of the uncured oil is combined with a curing catalyst (e.g., about 5 g uncured oil with about 4 wt. % dibutyl tin dilaurate) is cured in a closed chamber at a constant temperature and constant relative humidity for a fixed period (e.g., about 25° C. and about 100% relative humidity for about 2 days). The cured sample is extracted according to the foregoing procedure to determine the gel content.

Prior to use, the silane-modified oil is kept in a moisture-impervious packaging to maintain anhydrous conditions. In use, the composition can be brushed, sprayed, dipped, or otherwise applied onto a substrate by any common techniques using conventional equipment known in the art, and the resulting exposure to ambient moisture is sufficient to allow the composition to cure. The silane-modified oil also can be provided in a solution with a non-aqueous solvent (e.g., acetone, toluene, hexane) or in a suspension with a non-aqueous solvent (e.g., alcohols such as ethanol, methanol, and the like), which solution or suspension can optionally include the curing catalyst. The solution/suspension can then be sprayed onto a substrate to provide a thinner coating than might otherwise be possible with the concentrated silane-modified oil.

FIG. 1 illustrates the grafting and curing processes and resulting compositions for a triglyceride unsaturated oil molecule having an 18-carbon unsaturated aliphatic hydrocarbon chain (e.g., as a representative component of a fatty acid triglyceride) as one of the three fatty acid esters and vinyltrimethoxysilane (structure A). The grafting reaction (e.g., initiated by a peroxide free radical initiator, not shown) opens the vinyl group on the silane and grafts the silane to the aliphatic hydrocarbon chain (structure B). The hydrolysable silane is grafted to the aliphatic carbon chain at a position previously occupied by an olefinic carbon in the original oil. As a result of the grafting reaction, however, the carbon-carbon double bond migrates to an adjacent carbon-carbon pair (e.g., as illustrated in structures A and B). Thus, in the silane-modified oil, the hydrolysable silane is grafted to the carbon chain at a position displaced by one carbon from the migrated carbon-carbon double bond. Curing by exposure to water (e.g., atmospheric moisture) subsequently hydrolyzes the methoxy groups from the silicon, thereby forming silanol groups that can be further condensed with other silanol groups to form covalent intermolecular siloxane crosslinks in the cured product (structure C).

EXAMPLES

The following examples illustrate the disclosed compositions and methods, but are not intended to limit the scope of any claims thereto.

Example 1

Soybean oil (290 gr), vinyltrimethoxysilane (246 gr) and 2,5-bis(tert-butylperoxy)-2,5-dimethylhexane peroxide (LUPEROX 101) initiator (2.90 gr) were mixed in a closed flask. The mixture was pumped using a nitrogen blanket into a 2 L Parr hydrogenator (from Parr Instrument Company, Moline, Ill., USA) that was purged with nitrogen for 5 minutes prior to the introduction of the reaction mixture to ensure an anhydrous atmosphere. The temperature of the reactor was set to 160° C. and the agitation was kept at 200 rpm in order to mix the reactants and distribute heat uniformly in the system. Samples were withdrawn from the reactor periodically as shown in Table 1 ("Sample Initial Weight"). The samples were then analyzed in the TGA at 160° C. to volatilize and remove unreacted vinyltrimethoxysilane, and the post-volatilization weight of the sample also was recorded ("Sample Final Weight"). The amount of silane that was grafted with the soybean oil was determined by mass balance.

TABLE 1

Extent of reaction of vinyltrimethoxysilane with soybean oil at 160° C.

| Temperature (° C.)-Time (hrs) | Sample Initial wt. (mg) | Sample Final wt. (mg) | Silane grafted (wt % of total silane added) |
|---|---|---|---|
| 160-0 | 32.861 | 19.312 | 9.94 |
| 160-1 | 28.643 | 17.318 | 13.65 |
| 160-3 | 29.605 | 17.905 | 13.69 |
| 160-6 | 26.975 | 16.360 | 14.06 |
| 160-10 | 30.236 | 18.483 | 15.11 |

Example 2

Soybean oil (290 gr), vinyltrimethoxysilane (246 gr) and 2,5-bis(tert-butylperoxy)-2,5-dimethylhexane peroxide (LUPEROX 101) initiator (2.90 gr) were mixed in a closed flask as in Example 1. The temperature of the reactor was set to 180° C. and the agitation was kept at 200 rpm in order to mix the reactants and distribute heat uniformly in the system. Samples were withdrawn from the reactor periodically as shown in Table 2 and the amount of silane that was reacted with the oil was determined.

TABLE 2

Extent of reaction of vinyltrimethoxysilane with soybean oil at 180° C.

| Temperature (° C.)-Time (hrs) | Sample Initial wt. (mg) | Sample Final wt. (mg) | Silane grafted (wt % of total silane added) |
|---|---|---|---|
| 180-0 | 27.666 | 17.059 | 16.28 |
| 180-1 | 31.637 | 19.308 | 14.90 |
| 180-3 | 32.938 | 20.481 | 17.41 |
| 180-6 | 30.987 | 19.063 | 15.97 |
| 180-10 | 29.096 | 18.069 | 17.24 |

Example 3

Soybean oil (290 gr), vinyltrimethoxysilane (246 gr) and 2,5-bis(tert-butylperoxy)-2,5-dimethylhexane peroxide (LUPEROX 101) initiator (2.90 gr) were mixed in a closed flask as in Example 1. The temperature of the reactor was set to 200° C. and the agitation was kept at 200 rpm in order to mix the reactants and distribute heat uniformly in the system. Samples were withdrawn from the reactor periodically as shown in Table 3 and the amount of silane that was reacted with the oil was determined.

TABLE 3

Extent of reaction of vinyltrimethoxysilane with soybean oil at 200° C.

| Temperature (° C.)-Time (hrs) | Sample Initial wt. (mg) | Sample Final wt. (mg) | Silane grafted (wt % of total silane added) |
|---|---|---|---|
| 200-0 | 34.080 | 21.164 | 17.24 |
| 200-1 | 33.856 | 21.160 | 18.12 |
| 200-3 | 35.286 | 22.304 | 19.67 |
| 200-6 | 32.987 | 21.475 | 23.81 |
| 200-10 | 33.825 | 22.720 | 28.35 |

Example 4

Soybean oil (290 gr), vinyltrimethoxysilane (246 gr) and 2,5-bis(tert-butylperoxy)-2,5-dimethylhexane peroxide (LUPEROX 101) initiator (2.90 gr) were mixed in a closed flask as in Example 1. The temperature of the reactor was set to 220° C. and the agitation was kept at 200 rpm in order to mix the reactants and distribute heat uniformly in the system. Samples were withdrawn from the reactor periodically as shown in Table 4 and the amount of silane that was reacted with the oil was determined.

TABLE 4

Extent of reaction of vinyltrimethoxysilane with soybean oil at 220° C.

| Temperature (° C.)-Time (hrs) | Sample Initial wt. (mg) | Sample Final wt. (mg) | Silane grafted (wt % of total silane added) |
|---|---|---|---|
| 220-0 | 31.050 | 19.431 | 18.29 |
| 220-1 | 30.542 | 19.526 | 21.25 |
| 220-3 | 32.142 | 20.818 | 23.09 |
| 220-6 | 32.034 | 21.168 | 25.96 |
| 220-10 | 29.327 | 19.807 | 29.16 |

Example 5

Soybean oil (290 gr), vinyltrimethoxysilane (246 gr) and 2,5-bis(tert-butylperoxy)-2,5-dimethylhexane peroxide (LUPEROX 101) initiator (2.90 gr) were mixed in a closed flask as in Example 1. The temperature of the reactor was set to 240° C. and the agitation was kept at 200 rpm in order to mix the reactants and distribute heat uniformly in the system. Samples were withdrawn from the reactor periodically as shown in Table 5 and the amount of silane that was reacted with the oil was determined.

TABLE 5

Extent of reaction of vinyltrimethoxysilane with soybean oil at 240° C.

| Temperature (° C.)-Time (hrs) | Sample Initial wt. (mg) | Sample Final wt. (mg) | Silane grafted (wt % of total silane added) |
|---|---|---|---|
| 240-0 | 31.940 | 20.266 | 20.20 |
| 240-1 | 26.877 | 17.940 | 27.43 |
| 240-3 | 31.910 | 21.724 | 30.34 |
| 240-6 | 32.189 | 22.455 | 34.02 |
| 240-10 | 36.829 | 26.414 | 38.31 |

Figure 2:
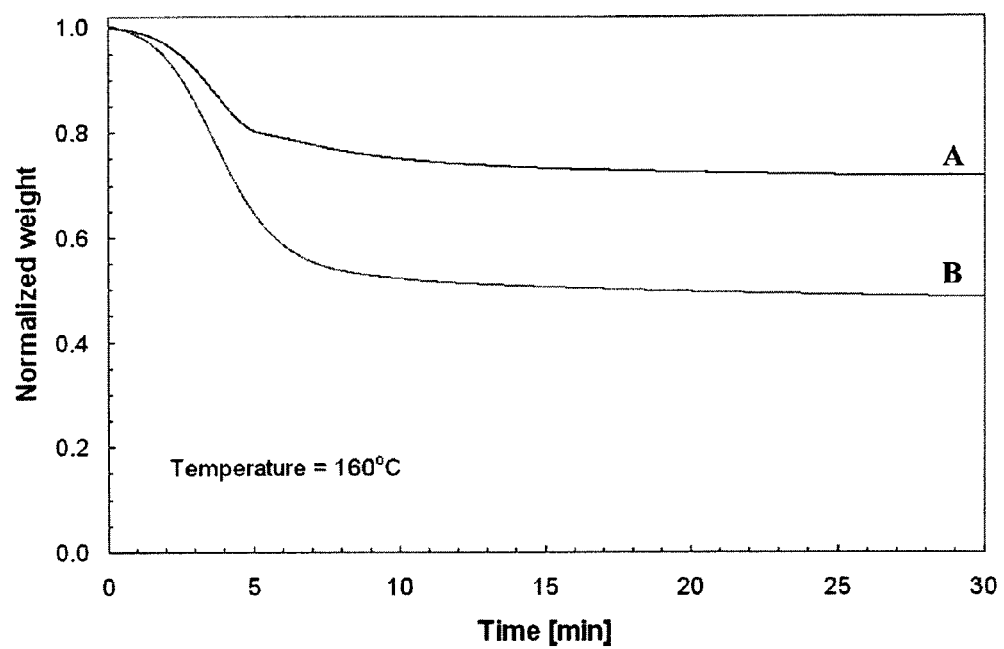
FIG. 2 is a graph representing the thermal gravimetric analysis of a silane-modified natural soybean oil according to the disclosure (line A) and a silane-modified natural soybean oil corresponding to Comparative Example 1 (line B).

The reaction product from Example 5 (after 10 hours of reaction time) was characterized by further analysis. For thermal gravimetric analysis (TGA), a small sample (about 25-30 mg) of the reaction product was heated to 160° C. under a nitrogen atmosphere and was maintained at this temperature for 30 minutes. The weight and the weight loss of the sample with time were recorded. Since the oil by itself does not exhibit any weight loss under these conditions, any weight loss is directly related to evaporation of unreacted (i.e., free) vinyltrimethoxysilane. FIG. 2 (line A) illustrates the TGA curve for the reaction product of Example 5. With an asymptotic TGA normalized weight of about 0.72, about 39 wt. % of the original vinyltrimethoxysilane had been grafted to the soybean oil, resulting in a silane-modified oil that contained about 25 wt. % of grafted silane.

Figure 3:
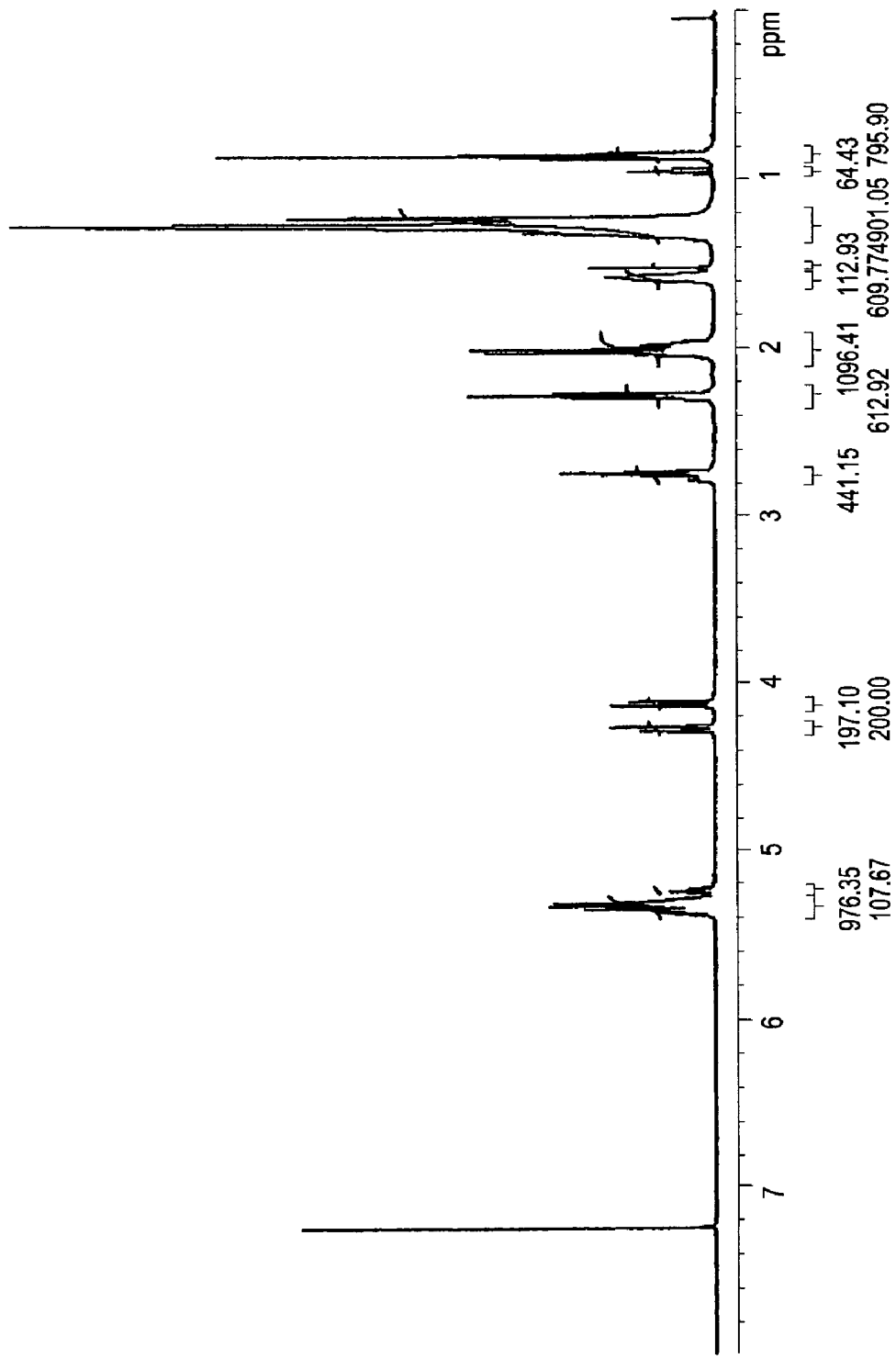
FIG. 3 is an $^1$H-NMR spectrum of an unmodified natural soybean oil.
Figure 4:
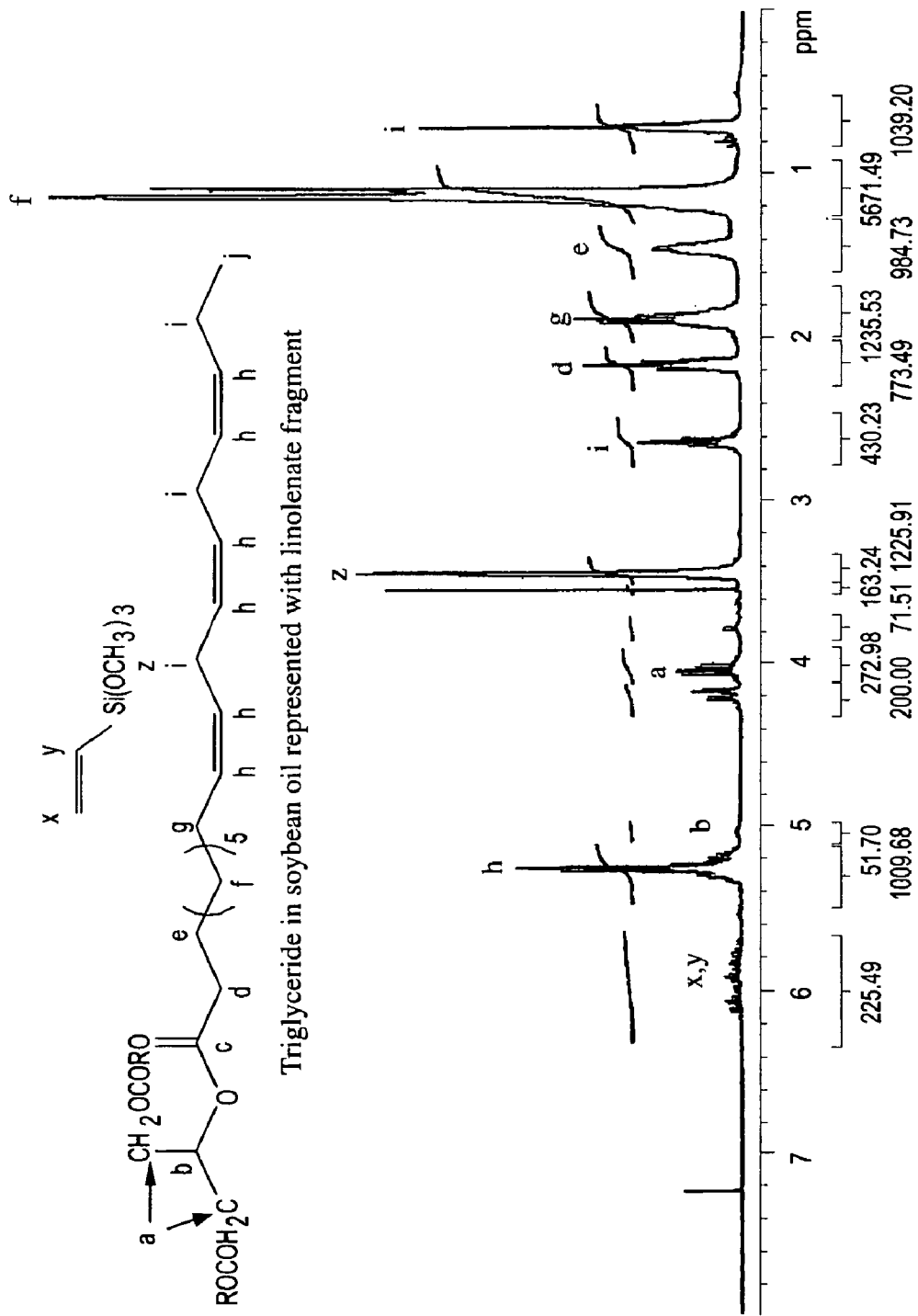
FIG. 4 is an $^1$H-NMR spectrum of a silane-modified natural soybean oil corresponding to the disclosure. The inset to FIG. 4 illustrates a linolenate side chain in a soybean oil triglyceride and the proton positions corresponding to the peaks in the NMR spectrum.

The reaction product from Example 5 was additionally analyzed to characterize the structure of the product. The product was heated to 130° C. and excess vinyltrimethoxysilane was removed by vacuum distillation. The resulting silane-modified oil was analyzed by $^1$H-NMR spectroscopy and then characterized to determine the loss of carbon-carbon double bonds (iodine value; mg KOH/g of sample as determined by ASTM D1959) and the increase in molecular weight by "bodying" (Brookfield viscosity). The original, unmodified soybean oil was similarly analyzed for comparison. FIGS. 3 and 4 present the $^1$H-NMR spectra of the unmodified soybean oil and the product of Example 5, respectively. Relevant peaks in the spectra are the olefinic protons attached to the carbon-carbon double bonds (at about 5.3 ppm) and the glyceryl methylene protons (at about 4.1 ppm and about 4.3 ppm); other characteristic peaks are labeled with their corresponding structures in FIG. 4. In Example 5, the iodine value of the silane-modified oil was 138 (compared to 148 for the unmodified soybean oil; a reduction of about 7%), and the viscosity of the silane-modified oil was 62 cPs (compared to 47 cPs for the unmodified soybean oil; an increase of about 32%). Thus, the disclosed catalytic process yields a composition that minimizes undesirable coupling reactions (e.g., bodying) between triglycerides while promoting grafting the vinylsilanes onto the triglycerides.

Comparative Example 1

Figure 5:
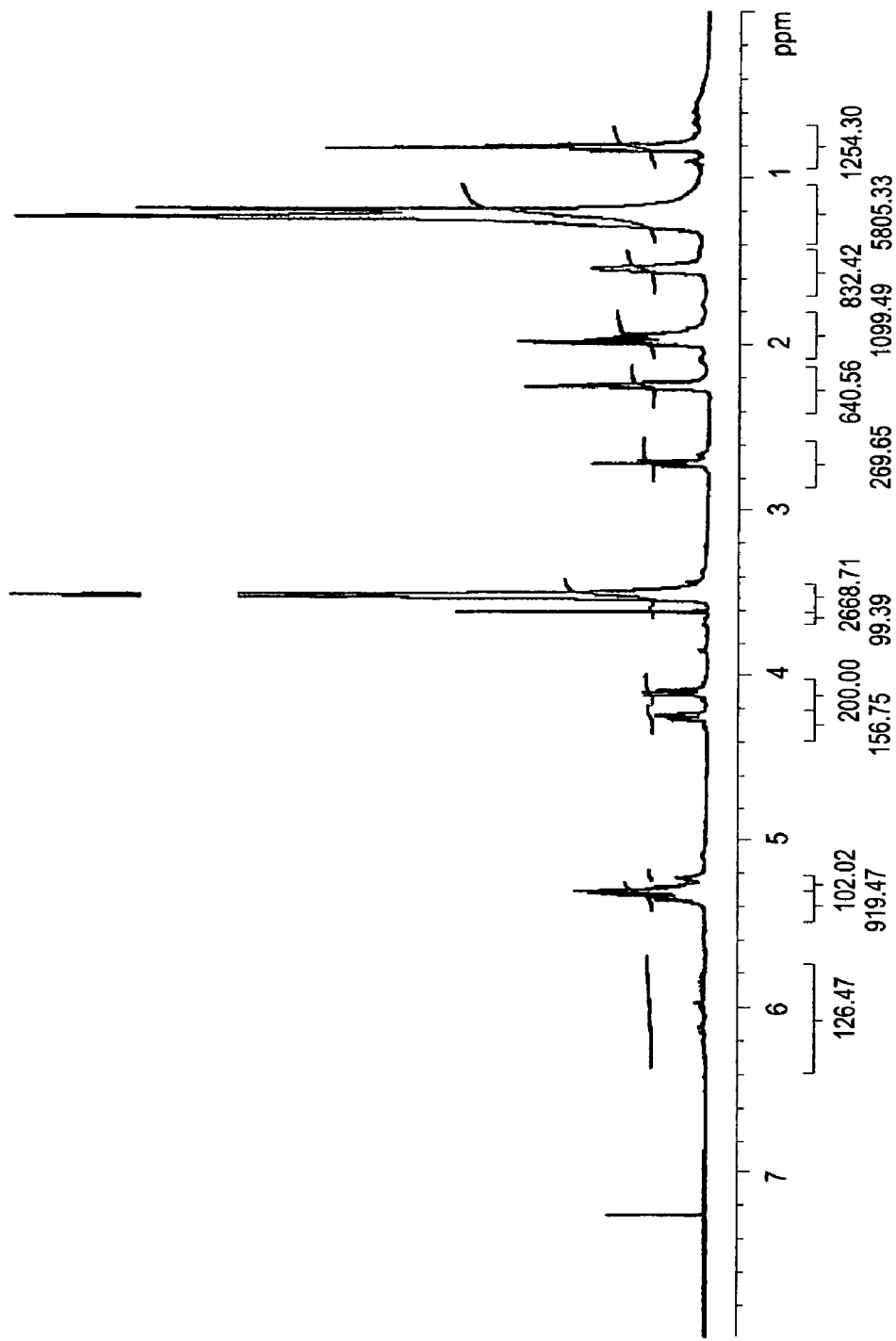
FIG. 5 is an $^1$H-NMR spectrum of a silane-modified natural soybean oil corresponding to Comparative Example 1.

A modified soybean oil was prepared according to the process of Kampf U.S. Pat. No. 4,512,926 (Example 24). Soybean oil (100 gr) and vinyltrimethoxysilane (200 gr) were charged into a Parr reactor. The reactor was heated under a nitrogen atmosphere and maintained at 270° C. for 5 hours with continuous agitation. The product was vacuum distilled at 130° C. for 1 hour, and the resulting residue was 150 gr, indicating that about 25 wt. % of the original vinyltrimethoxysilane had been grafted to the soybean oil, resulting in a modified oil that contained about 33 wt. % of grafted silane. This result was confirmed by thermal gravimetric analysis in a manner similar to Example 5, as illustrated in FIG. 2 (line B with an asymptotic TGA normalized weight of about 0.5). The $^1$H-NMR spectra of the modified soybean oil is presented in FIG. 5. The product of Comparative Example 1 had a significantly larger loss of double bonds and increase in viscosity as compared to Example 5: the iodine value of the modified soybean oil was 99 (compared to 148 for the unmodified soybean oil; a reduction of about 33%), and the viscosity of the modified soybean oil was 75 cPs (compared to 47 cPs for the unmodified soybean oil; an increase of about 62%).

The gel content of the reaction product also was determined. Specifically, about 2 g of the modified soybean oil was dissolved 40 ml hexane and 1 ml of 5% dibutyl tin dilaurate hexane. The oil/hexane mixture was added to water and allowed to stand for 24 hours at room temperature, thus forming a cured polymer film on the surface of the water. The cured polymer film was then dried at 50° C. for 24 hours. The gel content of dried, cured samples was then determined in both toluene (60% gel content) and chloroform (55% gel content) by adding about 1-2 g of a sample to 50 ml of each solvent and following the general gel content procedure outline above. Thus, a substantial portion of the soybean oil molecules do not contain grafted hydrolysable silanes that remain as an unreacted liquid in the cured sample (i.e., which can subsequently leach out of the cured sample).

Example 6

Tetraisopropyltitanate (0.2 gr) was added to a silylated soybean oil sample (5 ml) from Example 5 and was mixed well prior to curing. The sample was then poured into a Petri dish (about 2 mm in thickness) and was allowed to cure in a closed chamber at a constant temperature of 25° C. next to a container filled with water in order to achieve 100% relative humidity. Within 2 hours, a tack-free skin was observed and, after 2 days, the sample was completely cured, having a gel fraction greater than 90% as measured in 50 ml chloroform using a sample size of about 1-2 g.

Comparative Example 2

Samples were prepared as in Example 6, but without tetraisopropyltitanate. No significant cure was observed after 2 days under identical conditions as described in Example 6, and the sample remained low viscosity liquid.

Example 7

Samples containing dibutyl tin dilaurate (0.2 gr) and a silylated soybean oil sample (5 ml) from Example 5 were brushed onto wood, polystyrene, glass, cardboard, and wood panels to give a thin coating about 1 mm in thickness. The samples were then allowed to cure at ambient conditions (25° C. and about 35% relative humidity). After 2 days the surface of all the coatings appeared dry to the touch indicating complete cure. No uncured oil appeared on the surface of the coating or in the surrounding areas. In all cases excellent adhesion was observed between the coatings and the substrates.

Example 8

The silylated soybean oil obtained in Example 5 was brushed onto pine wood samples about 2"×2"×4" in size and allowed to cure for one day at ambient temperature followed by a post-cure at 50° C. for 24 hr. The coated samples and uncoated control pine wood samples were then placed in water and their water pick-up was determined periodically as shown in Table 6.

TABLE 6

| Water pick-up of pine wood samples | | |
|---|---|---|
| Time [hrs] | uncoated [wt %] | coated [wt %] |
| 0.00 | 0.0 | 0.0 |
| 0.05 | 15.1 | 0.7 |
| 0.10 | 22.5 | 1.3 |
| 0.15 | 26.7 | 1.5 |
| 0.20 | 29.3 | 1.5 |
| 0.25 | 31.1 | 1.6 |
| 0.30 | 32.8 | 1.8 |
| 0.38 | 34.7 | 2.0 |
| 0.47 | 36.1 | 2.2 |
| 0.63 | 37.6 | 2.4 |
| 2.09 | 43.6 | 3.9 |
| 4.90 | 51.9 | 5.1 |

Example 9

Stannous 2-ethyl hexanoate (0.3 gr) was added to the final sample obtained in Example 5 (5 ml). The sample was then cast into a petri dish, forming a 1 mm thick sample, and allowed to cure in an oven at 55° C. at 100% humidity. The sample showed a tack free time (TFT) of 3 hours and was completely cured after 1 day with no oil leachates observed on the top of the film.

Example 10

Dibutyl tin dilaurate (0.2 gr) was added to the sample in Example 5 (5 gr). The resulting sample was diluted with ethanol (50% by weight) and sprayed onto paper. The resulting samples had a thin coating of the oil (much less than 1 mm). These were allowed to cure at 25° C. at ambient humidity to yield a tack-free surface in less than 40 minutes. The paper had a glossy look and good water repellency.

Example 11

The silylated oil sample from Example 5 (5 gr) was mixed with 0.15, 0.25, and 0.5 gr of fumed silica having a size ranging from 0.007 μm to 0.014 μm. The resultant material was gel-like and could be cast into discs of 3 mm thickness or more. The samples, without any added curing catalyst, had a tack-free time of 3 hours. The samples were cured completely without any leachates on the surface after a period of 2 days at 25° C. at ambient humidity. The samples were rubbery to the touch and transparent.

Example 12

The samples from Example 11 were also drawn onto a 12"×12" glass plate using a polished glass rod to yield silica-reinforced coatings on glass. The tack free time in this case was about 1 hour and the resultant coatings exhibited excellent adhesion to glass and were translucent.

Example 13

Dibutyl tin dilaurate (0.2 gr) was added with the oil obtained from Example 5 (5 gr) and the resultant mixture brushed onto smooth rolled mild steel panels (2"×4"×0.02"), whose surface was degreased using acetone. No other priming of the steel surface was done prior to coating. The coatings had a thickness less than 1 mm. These were allowed to cure in an oven at 55° C. at 100% humidity. The cured oil had excellent adhesion to metal. The tack free time in this case was less than 45 minutes and complete cure was achieved without any surface leachates in 1 hour to yield transparent coatings.

Example 14

Coatings of curable samples in the aforementioned examples can also be formulated using water in the composition (e.g., about 0.25 g water/5 g composition; alternatively about 0.1 wt. % to about 10 wt. %, or about 1 wt. % to about 8 wt. % water relative to the weight of the silane-modified oil. Preferably, the water is added and mixed vigorously just before application of the silane-modified oil onto a substrate). The cure can be accomplished at ambient temperature with post-curing (e.g., at 50° C. for 24 hr).

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

Throughout the specification, where the compositions or processes are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

What is claimed is:

1. A moisture-curable, silane-modified oil comprising:
   (a) an unsaturated oil comprising at least one unsaturated aliphatic hydrocarbon chain per molecule of the unsaturated oil, and
   (b) a hydrolysable silyl group grafted to the unsaturated aliphatic hydrocarbon chain;
   wherein the silane-modified oil has a degree of unsaturation that is at least about 70% of that of the unsaturated oil; and
   wherein the molar ratio of grafted hydrolysable silyl groups to unsaturated oil molecules ranges from about 1.2 to about 5.

2. The moisture-curable, silane-modified oil of claim 1, wherein the hydrolysable silyl group is represented by Formula II:

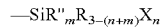

$$—SiR''_m R_{3-(n+m)} X_n \quad \text{[Formula II]}$$

wherein:
   (i) X is a hydrolysable functional group selected from the group consisting of alkoxy groups, aryloxy groups, carboxyloxy groups, halogens, and combinations thereof;
   (ii) R is selected from the group consisting of hydrogen, saturated aliphatic hydrocarbon groups, saturated alicyclic hydrocarbon groups, aryl hydrocarbon groups, heterocyclic hydrocarbon groups, and combinations thereof, the hydrocarbon groups containing from 1 to 30 carbon atoms;
   (iii) R" is selected from the group consisting of an unsaturated hydrocarbon residue containing from 2 to 30 carbon atoms, a graft reaction product thereof, and combinations thereof; and
   (iv) n ranges from 1 to 3, m ranges from 0 to 2, and n+m≦3.

3. The moisture-curable, silane-modified oil of claim 1, wherein the hydrolysable silyl group is selected from the group consisting of methoxy silyl groups, ethoxy silyl groups, acetoxy silyl groups, and combinations thereof.

4. The moisture-curable, silane-modified oil of claim 1, wherein the unsaturated oil comprises a triglyceride derived from one or more of soybean oil, safflower oil, linseed oil, corn oil, olive oil, sunflower oil, canola oil, sesame oil, cottonseed oil, palm oil, poppy-seed oil, peanut oil, coconut oil, rapeseed oil, tung oil, castor oil, fish oil, and whale oil.

5. The moisture-curable, silane-modified oil of claim 1, wherein the unsaturated oil comprises one or more unsaturated fatty acids having from 10 to 24 carbon atoms, esters thereof, monoglycerides thereof, and diglycerides thereof.

6. The moisture-curable, silane-modified oil of claim 1, wherein the silane-modified oil has an iodine number that is at least about 80% of that of the unsaturated oil.

7. The moisture-curable, silane-modified oil of claim 1, wherein substantially all of the unsaturated oil molecules have at least one hydrolysable silyl group grafted thereto via the unsaturated aliphatic hydrocarbon chain.

8. A composition comprising: a mixture comprising (a) the moisture-curable, silane-modified oil of claim 1, and (b) a curing catalyst selected from the group consisting of a titanium catalyst, a tin catalyst, and combinations thereof.

9. A process for curing a silane-modified oil, the process comprising: providing the silane-modified oil of claim 1; and
   curing the silane-modified oil with water, thereby hydrolyzing and condensing the hydrolysable silyl groups to form covalent intermolecular siloxane crosslinks in the silane-modified oil.

10. The process of claim 9, further comprising: prior to curing the silane-modified oil, applying the silane-modified oil to a substrate selected from the group consisting of glass, wood, paper, cement, metal, polymer, and combinations thereof.

11. The process of claim 9, further comprising: providing a curing catalyst to the silane-modified oil and the water, thereby accelerating the rate of intermolecular crosslink formation, wherein the curing catalyst is selected from the group consisting of a titanium catalyst, a tin catalyst, and combinations thereof.

12. The process of claim 11, wherein the silane-modified oil and the curing catalyst are provided as a mixture prior to exposure to water.

13. The process of claim 11, wherein the curing catalyst is selected from the group consisting of titanium naphthenate, tetraisopropyltitanate, tetrabutyltitanate, bis(acetylacetonyl)-diisopropyltitanate, tetra-2-ethylhexyl-titanate, tetraphenyltitanate, triethanolaminetitanate, organosiloxytitanium compounds, beta-dicarbonyl titanium compounds, dibutyl tin dilaurate, dibutyl tin diacetate, dioctyl tin dilaurate, tin octanoate, and combinations thereof.

14. The process of claim 9, wherein the water comprises atmospheric moisture.

15. A moisture-curable, silane-modified oil comprising:
(a) an unsaturated oil comprising at least one unsaturated aliphatic hydrocarbon chain per molecule of the unsaturated oil, and
(b) a hydrolysable silyl group grafted to the unsaturated aliphatic hydrocarbon chain;
wherein the silane-modified oil has a degree of unsaturation that is at least about 70% of that of the unsaturated oil; and
wherein the silane-modified oil has a gel content of at least about 70% once cured, and the silane-modified oil has a viscosity that is about 180% or less of that of the unsaturated oil.

16. A cured silane-modified oil comprising the reaction product of:
(a) a silane-modified oil comprising: (i) an unsaturated oil comprising at least one unsaturated aliphatic hydrocarbon chain per molecule of the unsaturated oil, and (ii) a hydrolysable silyl group grafted to the unsaturated aliphatic hydrocarbon chain; wherein the silane-modified oil has a degree of unsaturation that is at least about 70% of that of the unsaturated oil and the molar ratio of grafted hydrolysable silyl groups to unsaturated oil molecules ranges from about 1.2 to about 5; and
(b) water;
wherein:
(i) at least some of the hydrolysable silyl groups of the silane-modified oil have been hydrolyzed with the water and condensed, thereby forming covalent intermolecular siloxane crosslinks between silane-modified oil molecules in the cured silane-modified oil;
(ii) the cured silane-modified oil is sufficiently crosslinked with the intermolecular siloxane crosslinks to form a networked gel.

17. The cured silane-modified oil of claim 16, wherein the intermolecular siloxane crosslinks are represented by Formula III:

   [Formula III]

wherein:
(i) the Y moieties are independently selected from the group consisting of —OH, —R, —R", —O—Si(Y)$_2$—R'"—, and combinations thereof;
(ii) the R'" moieties are independently selected from the group consisting of hydrocarbon residues ranging from 2 to 30 carbon atoms;
(iii) R is selected from the group consisting of hydrogen, saturated aliphatic hydrocarbon groups, saturated alicyclic hydrocarbon groups, aryl hydrocarbon groups, heterocyclic hydrocarbon groups, and combinations thereof, the hydrocarbon groups containing from 1 to 30 carbon atoms; and
(iv) R" is selected from the group consisting of an unsaturated hydrocarbon residue containing from 2 to 30 carbon atoms, a graft reaction product thereof, and combinations thereof.

18. The cured silane-modified oil of claim 17, wherein:
(i) the unsaturated oil comprises soybean oil;
(ii) the Y moieties are independently selected from the group consisting of —OH, —O—Si(Y)$_2$—R'"—, and combinations thereof; and
(iii) the R'" moieties are independently selected from the group consisting of —CH$_2$CH$_2$—, —CH$_2$CH$_2$CH$_2$—, and combinations thereof.

19. The cured silane-modified oil of claim 16, wherein substantially all of the unsaturated oil molecules are crosslinked to at least one other unsaturated oil molecule via the intermolecular siloxane crosslinks.

20. A process for forming a moisture-curable, silane-modified oil, the process comprising:
reacting an unsaturated oil with an unsaturated hydrolysable silane in the presence of a free radical initiator to form a silane-modified oil comprising hydrolysable silyl groups grafted to the unsaturated oil.

21. The process of claim 20, wherein the unsaturated hydrolysable silane comprises a compound according to Formula I:

   [Formula I]

wherein:
(i) X is a hydrolysable functional group selected from the group consisting of alkoxy groups, aryloxy groups, carboxyloxy groups, halogens, and combinations thereof;
(ii) R is selected from the group consisting of hydrogen, saturated aliphatic hydrocarbon groups, saturated alicyclic hydrocarbon groups, aryl hydrocarbon groups, heterocyclic hydrocarbon groups, and combinations thereof, the hydrocarbon groups containing from 1 to 30 carbon atoms;
(iii) R" is an unsaturated hydrocarbon residue containing from 2 to 30 carbon atoms; and,
(iv) n ranges from 1 to 3, m ranges from 1 to 3, and n +m≦4.

22. The process of claim 21, wherein the unsaturated hydrolysable silane is polyunsaturated.

23. The process of claim 21, wherein R" is an aryl unsaturated hydrocarbon residue.

24. The process of claim 20, wherein the unsaturated hydrolysable silane is selected from the group consisting of vinyltrimethoxysilane, vinyltriethoxysilane, vinyltriacetoxysilane, allyldimethylacetoxysilane, allyltriisopropoxysilane, allylphenyldiphenoxysilane, and combinations thereof.

25. The process of claim 20, wherein the unsaturated oil comprises a triglyceride derived from one or more of soybean oil, safflower oil, linseed oil, corn oil, olive oil, sunflower oil, canola oil, sesame oil, cottonseed oil, palm oil, poppy-seed oil, peanut oil, coconut oil, rapeseed oil, tung oil, castor oil, fish oil, and whale oil.

26. The process of claim 20, wherein the unsaturated oil comprises one or more unsaturated fatty acids having from 10 to 24 carbon atoms, esters thereof, monoglycerides thereof, and diglycerides thereof.

27. The process of claim 20, wherein the free radical initiator comprises a thermal peroxide initiator selected from the group consisting of benzoyl peroxide, di-t-butylperoxide, 2,5-dimethyl-2,5-di (t-butylperoxide) hexane, bis-(methylbenzoyl)peroxide, bis(dimethylbenzoyl) peroxide, dicumylperoxide, t-butyl 3-isopropenylcumyl peroxide, butyl 4,4-bis(tert-butylperoxy)valerate, bis(trimethylbenzoyl)peroxide, and combinations thereof.

28. The process of claim 20, wherein, prior to reaction, the molar ratio of the unsaturated hydrolysable silane to the unsaturated oil ranges from about 2 to about 10, and the silane-modified oil has a viscosity that is about 180% or less of that of the unsaturated oil.

29. The process of claim 20, wherein the silane-modified oil has a gel content of at least about 70% once cured, and the silane-modified oil has a viscosity that is about 180% or less of that of the unsaturated oil.

30. The process of claim 20, wherein the silane-modified oil has an iodine number that is at least about 80% of that of the unsaturated oil.

31. The process of claim 20, comprising reacting the unsaturated oil with the unsaturated hydrolysable silane in the presence of the free radical initiator at a temperature ranging from about 100° C. to about 350° C. under an inert atmosphere that is substantially free from water.

\* \* \* \* \*